US007329643B2

(12) United States Patent
Tracey et al.

(10) Patent No.: US 7,329,643 B2
(45) Date of Patent: Feb. 12, 2008

(54) INHIBITION OF HMGB1 RELEASE BY FETUIN

(75) Inventors: Kevin J. Tracey, Old Greenwich, CT (US); Haicho Wang, Edison, NJ (US); Andrew E. Sama, Manhasset, NY (US)

(73) Assignee: The Feinstein Institute for Medical Research, Manhasset, NY (US)

(*) Notice: Subject to any disclaimer, the term of this patent is extended or adjusted under 35 U.S.C. 154(b) by 0 days.

(21) Appl. No.: 11/129,672

(22) Filed: May 13, 2005

(65) Prior Publication Data

US 2006/0258579 A1 Nov. 16, 2006

Related U.S. Application Data

(60) Provisional application No. 60/571,343, filed on May 14, 2004.

(51) Int. Cl.
*A61K 38/17* (2006.01)
*C07K 14/00* (2006.01)

(52) U.S. Cl. .......................................... 514/8; 530/395

(58) Field of Classification Search .................... 514/2, 514/8; 435/7.1; 530/395
See application file for complete search history.

(56) References Cited

U.S. PATENT DOCUMENTS 6,117,837 A * 9/2000 Tracey et al. .................. 514/2

OTHER PUBLICATIONS

Chen, G., et al. 2004 Acad Emerg Med 11(5): 531-532.*
Dziegielewska, K.M., et al. 1998 Biol. of the Neonate 74(5): 372-375.*
Alzheimer's Disease 2001 R&D Systems Catalog.*
Gandhi, R., et al. 1999 Life Cycle of HIV Infection (article). Hopkins AIDS Service.*
Babakhanian, R. 1995 AIDS Treatment Update (article).*
Dziegielewska, K.M., et al. 1998 Biol Neonate 74: 372-375.*
Dziegielewska, K.M., et al. 1998 Immunology Letters 60: 31.35.*
Abraham, E. et al. 2000. "Cutting Edge: HMG-1 as a mediator of acute lung inflammation." J Immunol. 165:2950-2954.
Agnello, D. et al. 2002. "HMGB1, a DNA-binding protein with cytokine activity, induces brain TNF and IL-6 production, and mediates anorexia and taste aversion." Cytokine. 18:231-236.
Akhoundi, C. et al. 1994. "Insulin and interleukin-1 differentially regulate pp63, an acute phase phosphoprotein in hepatoma cell line." J Biol Chem. 269:15925-15930.
Andersson, U., et al. 2000. "High Mobility Group 1 Protein (HMG-1) Stimulates Proinflammatory Cytokine Synthesis in Human Monocytes." J Exp Med. 192:565-570.

Daveau, m., et al. 1988. "The synthesis of human alpha-2-HS glycoprotein is down-regulated by cytokines in hepatoma HepG2 cells." FEBS Lett. 241:191-194.
Degryse, B., et al. 2001. "The high mobility group (HMG) boxes of the nuclear protein HMG1 induce chemotaxis and cytoskeleton reorganization in rat smooth muscle cells." J Cell Biol. 152:1197-1206.
Demetriou, M., et al. 1996. "Fetuin/alpha2-HS glycoprotein is a transforming growth factor-beta type II receptor mimic and cytokine antagonist." J Biol Chem. 271:12755-12761.
Haasemann, M., et al. 1991. "Rat tyrosine kinase inhibitor shows sequence similarity to human alpha 2-HS glycoprotein and bovine fetuin." Biochem J. 274:899-902.
Kokkola, R., et al. 2002. "High mobility group box chromosomal protein 1: a novel proinflammatory mediator in synovitis." Arthritis Rheum. 46:2598-2603.
Lebreton, J.P., et al. 1979. "Serum concentration of human alpha 2 HS glycoprotein during the inflammatory process: evidence that alpha 2 HS glycoprotein is a negative acute-phase reactant." J clin Invest. 64:1118-1129.
Li, J., et al. 2003. "Structural basis for the proinflammatory cytokine activity of high mobility group box 1." Mol.Med. 9:37-45.
Lin, X., et al. 1998. "Differential expression of insulin receptor tyrosine kinase inhibitor (fetuin) gene in a model of diet-induced obesity." Life Sci. 63:145-153.
Mathews, S.T., et al. 1997. "Bovine fetuin is an inhibitor of insulin receptor tyrosine kinase." Life Sci. 61:1583-1592.
Ombrellino, M., et al. 1999. "Increased serum concentrations of high-mobility-group protein 1 in haemorrhagic shock [letter]." Lancet. 354:1446-1447.
Rendon-Mitchell, B., et al. 2003. "IFN-gamma induces High Mobility Group Box 1 protein Release Partly Through a TNF- Dependent Mechanism." J Immunol. 170:3890-3897.
Sappington, P.L., et al. 2002. "HMGB 1 B box increases the permeability of Caco-2 enterocytic monolayers and impairs intestinal barrier function in mice." Gastroenterology. 123:790-802.

(Continued)

*Primary Examiner*—Maryam Monshipouri
*Assistant Examiner*—Marsha Tsay
(74) *Attorney, Agent, or Firm*—Amster, Rothstein & Ebenstein LLP

(57) ABSTRACT

Methods of inhibiting HMGB1 release by a mammalian cell are provided. The methods comprise treating the cell with sufficient fetuin to inhibit HMGB1 release. Methods of inhibiting an inflammatory cytokine cascade in a mammal are also provided. These methods comprise administering sufficient fetuin to the mammal to inhibit HMGB1 release in the mammal. Also provided are methods of treating a condition in a mammal characterized by an inflammatory cytokine cascade. These methods comprise administering sufficient fetuin to the mammal to inhibit HMGB1 release in the mammal.

8 Claims, 6 Drawing Sheets

OTHER PUBLICATIONS

Scaffidi, P., et al. 2002. "Release of chromatin protein HMGB1 by necrotic cells triggers inflammation," Nature. 418:191-195.

Suzuki, M., et al. 1994. "Calcium-binding properties of fetuin in fetal bovine serum." J Exp Zool. 270:501-507.

Taniguchi, N., et al. 2003. "High mobility group box chromosomal protein 1 plays a role in the pathogenesis of rheumatoid arthritis as a novel cytokine." Arthritis Rheum. 48-971-981.

Ulloa, L., et al. 2002. "Ethyl pyruvate prevents lethality in mice with established lethal sepsis and systemic inflammation." Proc Natl Acad Sci U S A. 99:12351-12356.

Wang, H., et al. 1999. "HMG-1 as a late mediator of endotoxin lethality in mice." Science. 285:248-251.

Wang, H., et al. 2003. "HMGB1." pp. 913-923 in A. Thomson and M.T. Lotze, editors, The Cytokine Handbook (4th Edition). Academic Press. pp. 913-923.

Wang, H. et al. 1999. "Fetuin opsonizes macrophage-deactivating cations." In J.C. Marshall and J. Cohen, editors, Update in Intensive Care and Emergency Medicine: Immune Response in the Critically Ill. SpringerVerlag Press. 155-163.

Wang, H. et al. 1999. "Proinflammatory cytokines (tumor necrosis factor and interleukin 1) stimulate release of high mobility group protein-1 by pituicytes." Surgery. 126:389-392.

Wang, H., et al. 1998. "Fetuin (alpha2-HS-glycoprotein) opsonizes cationic macrophage deactivating molecules." Proc Natl Acad Sci U S A. 95:14429-14434.

Wang, H., et al. 1997. "Fetuin protects the fetus from TNF [letter]." Lancet. 350:861-862.

Yang, H., et al. 2004. Reversing established sepsis with antagonists of endogenous high-mobility group box 1. Proc.Natl.Acad.Sci U.S.A. 101:296-301.

* cited by examiner

INHIBITION OF HMGB1 RELEASE BY FETUIN

CROSS-REFERENCE TO RELATED APPLICATION

This application claims the benefit of U.S. Provisional Application No. 60/571,343, filed May 14, 2004.

STATEMENT REGARDING FEDERALLY SPONSORED RESEARCH OR DEVELOPMENT

This invention was made with government support under Grant No. GM063075 awarded by The National Institutes of Health. The government has certain rights in the invention.

BACKGROUND (1) Field of the Invention

The present invention generally relates to methods of inhibiting inflammation. More specifically, the invention is directed to methods of inhibiting an inflammatory cytokine cascade by inhibiting HMGB1 release.

(2) Description of the Related Art

REFERENCES CITED

Abraham, E., J. Arcaroli, A. Carmody, H. Wang, and K. J. Tracey. 2000. "HMG-1 as a mediator of acute lung inflammation." *J Immunol.* 165:2950-2954.

Agnello, D., H. Wang, H. Yang, K. J. Tracey, and P. Ghezzi. 2002. "HMGB1, a DNA-binding protein with cytokine activity, induces brain TNF and IL-6 production, and mediates anorexia and taste aversion." *Cytokine.* 18:231-236.

Akhoundi, C., M. Amiot, P. Auberger, A. Le Cam, and B. Rossi. 1994. "Insulin and interleukin-1 differentially regulate pp 63, an acute phase phosphoprotein in hepatoma cell line." *J Biol Chem.* 269:15925-15930.

Andersson, U., H. Wang, K. Palmblad, A. C. Aveberger, O. Bloom, H. Erlandsson-Harris, A. Janson, R. Kokkola, M. Zhang, H. Yang, and K. J. Tracey. 2000. "High Mobility Group 1 Protein (HMG-1) Stimulates Proinflammatory Cytokine Synthesis in Human Monocytes." *J Exp Med.* 192:565-570.

Bustin, M. 2001. "Revised nomenclature for high mobility group (HMG) chromosomal proteins." *Trends Biochem Sci.* 26:152-153.

Daveau, M., D. Christian, N. Julen, M. Hiron, P. Arnaud, and J. P. Lebreton. 1988. "The synthesis of human alpha-2-HS glycoprotein is down-regulated by cytokines in hepatoma HepG2 cells." *FEBS Lett.* 241:191-194.

Daveau, M., C. Davrinche, N. Djelassi, J. Lemetayer, N. Julen, M. Hiron, P. Arnaud, and J. P. Lebreton. 1990. "Partial hepatectomy and mediators of inflammation decrease the expression of liver alpha 2-HS glycoprotein gene in rats." *FEBS Lett.* 273:79-81.

Degryse, B., T. Bonaldi, P. Scaffidi, S. Muller, M. Resnati, F. Sanvito, G. Arrigoni, and M. E. Bianchi. 2001. "The high mobility group (HMG) boxes of the nuclear protein HMG1 induce chemotaxis and cytoskeleton reorganization in rat smooth muscle cells." *J. Cell Biol.* 152:1197-1206.

Demetriou, M., C. Binkert, B. Sukhu, H. C. Tenenbaum, and J. W. Dennis. 1996. "Fetuin/alpha2-HS glycoprotein is a transforming growth factor-beta type II receptor mimic and cytokine antagonist." *J Biol Chem.* 271:12755-12761.

Dziegielewska, K. M., Y. Daikuhara, T. Ohnishi, M. P. Waite, J. Ek, M. D. Habgood, M. A. Lane, A. Potter, and N. R. Saunders. 2000. "Fetuin in the developing neocortex of the rat: distribution and origin." *J Comp Neurol.* 423:373-388.

Ferrari, S., P. Finelli, M. Rocchi, and M. E. Bianchi. 1996. "The active gene that encodes human high mobility group 1 protein (HMG1) contains introns and maps to chromosome 13." *Genomics.* 35:367-371.

Ferrari, S., L. Ronfani, S. Calogero, and M. E. Bianchi. 1994. "The mouse gene coding for high mobility group 1 protein (HMG1)." *J Biol Chem.* 269:28803-28808.

Gariboldi, M., L. De Gregorio, S. Ferrari, G. Manenti, M. A. Pierotti, M. E. Bianchi, and T. A. Dragani. 1995. "Mapping of the Hmg1 gene and of seven related sequences in the mouse." *Mamm Genome.* 6:581-585.

Haasemann, M., P. Nawratil, and W. Muller-Esterl. 1991. "Rat tyrosine kinase inhibitor shows sequence similarity to human alpha 2-HS glycoprotein and bovine fetuin." *Biochem J.* 274:899-902.

Johns, E. W. 1982. "History, Definitions and Problems." In E. W. Johns, editor, *The HMG Chromosomal Proteins.* Academic Press Inc. (London) Ltd. London. 1-8.

Kitchener, P. D., K. M. Dziegielewska, E. J. Hutton, C. F. Hinrichsen, and N. R. Saunders. 1999. "Fetuin in neurons of the retina and cerebellum during fetal and postnatal development of the rat." *Int J Dev Neurosci.* 17:21-30.

Kitchener, P. D., K. M. Dziegielewska, G. W. Knott, J. M. Miller, P. Nawratil, A. E. Potter, and N. R. Saunders. 1997. "Fetuin expression in the dorsal root ganglia and trigeminal ganglia of perinatal rats." *Int. J Dev. Neurosci.* 15:717-727.

Kokkola, R., E. Sundberg, A. K. Ulfgren, K. Palmblad, J. Li, H. Wang, L. Ulloa, H. Yang, X. J. Yan, N. Chiorazzi, K. J. Tracey, U. Andersson, and H. E. Harris. 2002a. "High mobility group box chromosomal protein 1: a novel proinflammatory mediator in synovitis." *Arthritis Rheum.* 46:2598-2603.

Kokkola, R., E. Sundberg, A. K. Ulfgren, K. Palmblad, J. Li, H. Wang, L. Ulloa, H. Yang, X. J. Yan, R. Furie, N. Chiorazzi, K. J. Tracey, U. Andersson, and H. E. Harris. 2002b. "High mobility group box chromosomal protein 1: a novel proinflammatory mediator in synovitis." *Arthritis Rheum.* 46:2598-2603.

Landsman, D. and M. Bustin. 1993. "A signature for the HMG-1 box DNA-binding proteins." *Bioessays.* 15:539-546.

Lebreton, J. P., F. Joisel, J. P. Raoult, B. Lannuzel, J. P. Rogez, and G. Humbert. 1979. "Serum concentration of human alpha 2 HS glycoprotein during the inflammatory process: evidence that alpha 2 HS glycoprotein is a negative acute-phase reactant." *J Clin Invest.* 64:1118-1129.

Li, J., R. Kokkola, S. Tabizadeh, R. Yang, M. Ochani, X. Qiang, H. E. Harris, C. J. Czura, H. Wang, L. Ulloa, H. Wang, H. S. Warren, L. L. Moldawer, M. P. Fink, U. Andersson, K. J. Tracey, and H. Yang. 2003. "Structural basis for the proinflammatory cytokine activity of high mobility group box 1." *Mol. Med.* 9:37-45.

Lin, X., H. D. Braymer, G. A. Bray, and D. A. York. 1998. "Differential expression of insulin receptor tyrosine kinase inhibitor (fetuin) gene in a model of diet-induced obesity." *Life Sci.* 63:145-153.

Mathews, S. T., P. R. Srinivas, M. A. Leon, and G. Grunberger. 1997. "Bovine fetuin is an inhibitor of insulin receptor tyrosine kinase." *Life Sci.* 61:1583-1592.

Mosevitsky, M. I., V. A. Novitskaya, M. G. Iogannsen, and M. A. Zabezhinsky. 1989. "Tissue specificity of nucleocytoplasmic distribution of HMG1 and HMG2 proteins and their probable functions." *Eur J Biochem.* 185:303-310.

Ombrellino, M., H. Wang, M. S. Ajemian, A. Talhouk, L. A. Scher, S. G. Friedman, and K. J. Tracey. 1999. "Increased serum concentrations of high-mobility-group protein 1 in haemorrhagic shock [letter]." *Lancet.* 354:1446-1447.

Paonessa, G., R. Frank, and R. Cortese. 1987. "Nucleotide sequence of rat liver HMG1 cDNA." *Nucleic Acids Res.* 15:9077.

Pedersen, K. O. 1944. "Fetuin, a new globin isolated from serum." *Nature.* 154:575-570.

Prasad, S. and M. K. Thakur. 1988. "Age-dependent effects of sodium butyrate and hydrocortisone on acetylation of high mobility group proteins of rat liver." *Biochem Int.* 16:375-382.

Rendon-Mitchell, B., M. Ochani, J. Li, J. Han, H. Wang, H. Yang, S. Susarla, C. Czura, R. A. Mitchell, G. Chen, A. E. Sama, K. J. Tracey, and H. Wang. 2003. "IFN-gamma Induces High Mobility Group Box 1 Protein Release Partly Through a TNF-Dependent Mechanism." *J Immunol.* 170: 3890-3897.

Sappington, P. L., R. Yang, H. Yang, K. J. Tracey, R. L. Delude, and M. P. Fink. 2002. "HMGB1 B box increases the permeability of Caco-2 enterocytic monolayers and causes derangements in intestinal barrier function in mice." *Gastroenterology.* 123:790-802.

Scaffidi, P., T. Misteli, and M. E. Bianchi. 2002. "Release of chromatin protein HMGB1 by necrotic cells triggers inflammation." *Nature.* 418:191-195.

Schinke, T., C. Amendt, A. Trindl, O. Poschke, W. Muller-Esterl, and W. Jahnen-Dechent. 1996. "The serum protein alpha2-HS glycoprotein/fetuin inhibits apatite formation in vitro and in mineralizing calvaria cells. A possible role in mineralization and calcium homeostasis." *J Biol Chem.* 271:20789-20796.

Suzuki, M., H. Shimokawa, Y. Takagi, and S. Sasaki. 1994. "Calcium-binding properties of fetuin in fetal bovine serum." *J Exp Zool.* 270:501-507.

Szweras, M., D. Liu, E. A. Partridge, J. Pawling, B. Sukhu, C. Clokie, W. Jahnen-Dechent, H. C. Tenenbaum, C. J. Swallow, M. D. Grynpas, and J. W. Dennis. "alpha 2-HS glycoprotein/fetuin, a transforming growth factor-beta/bone morphogenetic protein antagonist, regulates postnatal bone growth and remodeling." *J Biol Chem* 2002. May 31; 277.(22):19991.-7. 277:19991-19997.

Taniguchi, N., K. Kawahara, K. Yone, T. Hashiguchi, M. Yamakuchi, M. Goto, K. Inoue, S. Yamada, K. Ijiri, S. Matsunaga, T. Nakajima, S. Komiya, and I. Maruyama. 2003. "High mobility group box chromosomal protein 1 plays a role in the pathogenesis of rheumatoid arthritis as a novel cytokine." *Arthritis Rheum.* 48:971-981.

Terkelsen, O. B., W. Jahnen-Dechent, H. Nielsen, T. Moos, E. Fink, P., Nawratil, W. Muller-Esterl, and K. Mollgard. 1998. "Rat fetuin: distribution of protein and mRNA in embryonic and neonatal rat tissues." *Anat. Embryol.* (Berl). 197:125-133.

Ulloa, L., M. Ochani, H. Yang, M. Tanovic, D. Halperin, R. Yang, C. J. Czura, M. P. Fink, and K. J. Tracey. 2002. "Ethyl pyruvate prevents lethality in mice with established lethal sepsis and systemic inflammation." *Proc Natl Acad Sci USA.* 99:12351-12356.

Wang, H., O. Bloom, M. Zhang, J. M. Vishnubhakat, M. Ombrellino, J. Che, A. Frazier, H. Yang, S. Ivanova, L. Borovikova, K. R. Manogue, E. Faist, E. Abraham, J. Andersson, U. Andersson, P. E. Molina, N. N. Abumrad, A. Sama, and K. J. Tracey. 1999a. "HMG-1 as a late mediator of endotoxin lethality in mice." *Science.* 285:248-251.

Wang, H., C. J. Czura, and K. J. Tracey. 2003. "HMGB1." Pages 913-923 In A. Thomson and M. T. Lotze, editors, *The Cytokine Handbook* (4th Edition). Academic Press. Pp. 913-923.

Wang, H. and K. J. Tracey. 1999. "Fetuin opsonizes macrophage-deactivating cations." In J. C. Marshall and J. Cohen, editors, *Update in Intensive Care and Emergency Medicine: Immune Response in the Critically Ill.* SpringerVerlag Press. 155-163.

Wang, H., J. M. Vishnubhakat, O. Bloom, M. Zhang, M. Ombrellino, A. Sama, and K. J. Tracey. 1999b. "Proinflammatory cytokines (tumor necrosis factor and interleukin 1) stimulate release of high mobility group protein-1 by pituicytes." *Surgery.* 126:389-392.

Wang, H., M. Zhang, M. Bianchi, B. Sherry, A. Sama, and K. J. Tracey. 1998. "Fetuin (alpha2-HS-glycoprotein) opsonizes cationic macrophagedeactivating molecules." *Proc Natl Acad Sci USA.* 95:14429-14434.

Wang, H., M. Zhang, K. Soda, A. Sama, and K. J. Tracey. 1997. "Fetuin the fetus from TNF [letter]." *Lancet.* 350:861-862.

Wen, L., J. K. Huang, B. H. Johnson, and G. R. Reeck. 1989. "A human placental cDNA clone that encodes nonhistone chromosomal protein HMG-1." *Nucleic Acids Res.* 17:1197-1214.

Yang, H., M. Ochani, J. Li, X. Qiang, M. Tanovic, H. E. Harris, S. M. Susarla, L. Ulloa, H. Wang, R. DiRaimo, C. J. Czura, H. Wang, J. Roth, H. S. Warren, M. P. Fink, M. J. Fenton. U. Andersson, and K. J. Tracey. 2004. Reversing established sepsis with antagonists of endogenous highmobility group box 1. *Proc. Natl. Acad. Sci U.S.A.* 101:296-301.

HMGB1

Approximately 30 years ago, HMGB1 was first co-purified from nuclei with histones, and termed "high mobility group" (HMG) protein because of its rapid mobility on electrophoresis gels (Johns 1982). HMGB1 proteins are among the most ubiquitous, abundant, and evolutionarily conserved proteins in eukaryotes. As a highly conserved protein, HMGB1 shares 100% identity in amino acid sequence between mouse and rat, and a 99% amino acid identity between rodent and human (Ferrari et al. 1994; Paonessa et al. 1987; Wen et al. 1989)., Recently, HMG-1 was renamed as HMGB1 by a nomenclature committee (Bustin 2001). In mice, the Hmgb1 gene resides on chromosome 5 (Gariboldi et al. 1995), while in humans the gene lies on chromosome (Ferrari et al. 1996). HMGB1 is produced by nearly all cell types, but cellular levels vary with development and (Prasad and Thakur 1988). Cellular localization studies have revealed that HMGB1 is a cytoplasmic protein that can migrate between the cytoplasm and nucleus in a cell-cycle dependent fashion. Lymphoid cells contain significantly elevated levels of HMGB1 in both cytoplasm and (Landsman and Bustin 1993), whereas cells in liver and brain tissues contain HMGB1 predominantly in the (Mosevitsky et al. 1989).

In response to stimulation with exogenous bacterial endotoxin (e.g., lipopolysaccharide, LPS) or endogenous proinflammatory cytokines (such as TNF, IL-1β, and IFN-γ), cultures of macrophage, monocytes, and pituicytes actively release HMGB1 in a time- and dose-dependent (Rendon-Mitchell et al. 2003; Wang et al. 1999b; Wang et al. 1999a). In addition to the active release by activated innate immune cells, HMGB1 can also be passively released by necrotic or damaged (Degryse et al. 2001; Scaffidi et al. 2002). HMGB1 released by necrotic cells is capable of inducing an inflammatory response, and thereby transmitting the "injury" signal to its neighboring immune cells (Scaffidi et al. 2002). Therefore, extracellular HMGB1 functions as a late mediator of lethal systemic inflammation (e.g., endotoxemia and sepsis (Wang et al. 3 A. D.; Wang et al. 1999a). HMGB1 is released late by endotoxin-stimulated macrophages, and its serum levels increase significantly between 16 to 32 hours after endotoxemia and sepsis, a time frame that is delayed relative to TNF and IL-1β (Wang et al. 1999a; Yang et al. 2003). Elevated levels of HMGB1 are found in serum of patients with sepsis-induced organ failure hemorrhagic shock (Ombrellino et al. 1999; Wang et al. 1999a), and synovial fluid of patients with rheumatoid arthritis (Kokkola et al. 2002b; Kokkola et al. 2002a; Taniguchi et al. 2003). HMGB1 is defined as a cytokine because it activates various cellular responses, including chemotactic cell movement (Degryse et al. 2001), permeability of endothelial (Caco-2) enterocytic monolayers (Sappington et al. 2002), and the release of various proinflammatory cytokines (such as TNF, IL-1) (Abraham et al. 2000; Andersson et al. 2000), and nitric oxide (Sappington et al. 2002). Peripheral administration of exogenous HMGB1 to animals causes derangements in intestinal barrier function (Sappington et al. 2002), tissue injury (Abraham et al. 2000), and even lethality (Wang et al. 1999a). Direct intracerebral administration of HMGB1 induces fever, local production of proinflammatory cytokines (e.g., TNF, IL-6), and sickness behavior in animals (Agnello et al. 2002). Anti-HMGB1 antibodies significantly protect against lethal endotoxemia and LPS-induced acute lung injury, even when antibody administration is delayed until after the early TNF response (Abraham et al. 2000; Wang et al. 1999a). More recently, the important role of HMGB1 as late mediator of sepsis has been established in an animal model of sepsis (cecal ligation and puncture) (Yang et al. 2003). Anti-HMGB1 antibodies confer significant protection in an animal model of cecal perforation, even when antibody administration is delayed by 24 hours (Li et al. 2003). Because the therapeutic windows for anti-HMGB1 therapies are significantly wider than TNF-targeted interventions, it is thus possible to develop inhibitors of HMGB1 for treatment of systemic inflammation. For instance, suppression of HMGB1 release with anti-inflammatory compounds (such as ethyl pyruvate) also protects animals in a model of lethal systemic inflammation (i.e., cecal ligation and puncture) (Ulloa et al. 2002), suggesting that therapeutic agents targeting HMGB1 may prove useful in the treatment of inflammatory diseases.

Fetuin

Fetuin was first isolated by Pederson more than fifty years ago as a major plasma protein in fetus (Pedersen 1944). Although fetuin is produced by multiple organs (including liver, kidney and brain) during fetal development (Dziegielewska et al. 2000; Kitchener et al. 1997; Kitchener et al. 1999; Pedersen 1944; Terkelsen et al. 1998), it is produced primarily by the liver in the adult. The circulating levels of fetuin and its human homologue ($\alpha_2$-HS-glycoprotein) are significantly lower in adults than fetus, and can be further decreased during inflammation (Akhoundi et al. 1994), leading to the classification of fetuin as (Daveau et al. 1990) a negative acute phase protein (Daveau et al. 1988; Lebreton et al. 1979). We have recently discovered that fetuin occupies an important role in the regulation of the innate immune response by opsonizing cationic immunosuppressive molecules (such as spermine and CNI-1493) (Suzuki et al. 1994; Wang et al. 1997; Wang et al. 1998; Wang and Tracey 1999). The terminal sugar residue of the oligosaccharides is usually a sialic acid, which bears a net negative charge at physiological pH, and may be responsible for the binding to cationic molecules (such as spermine) (Wang et al. 1997; Wang et al. 1998). In addition to its immunosuppressive role, fetuin shares amino acid sequence similarity to insulin receptor tyrosine kinase (Haasemann et al. 1991; Lin et al. 1998; Mathews et al. 1997) and type II TGF-β receptor (Demetriou et al. 1996), and has thus been proposed as a natural inhibitor of the insulin signaling pathway and an antagonist of TGF-β (Demetriou et al. 1996). Furthermore, fetuin functions as a modulator of apatite formation during mineralization (Schinke et al. 1996), and occupies an important role in bone formation (Szweras et al. 2002). However, the potential role of fetuin itself in regulation of HMGB1 release is previously unknown.

SUMMARY OF THE INVENTION

The present invention is based on the discovery that fetuin inhibits the release of HMGB1 by mammalian cells, and that this inhibition can be used to inhibit inflammatory cytokine cascades in mammals.

Accordingly, in some embodiments, the invention is directed to methods of inhibiting HMGB1 release by a mammalian cell. The methods comprise treating the cell with sufficient fetuin to inhibit HMGB1 release.

In other embodiments, the invention is directed to methods of inhibiting an inflammatory cytokine cascade in a mammal. The methods comprise administering sufficient fetuin to the mammal to inhibit HMGB1 release in the mammal.

Additionally, the invention is directed to methods of treating a condition in a mammal characterized by an inflammatory cytokine cascade. The methods comprise administering sufficient fetuin to the mammal to inhibit HMGB1 release in the mammal.

DETAILED DESCRIPTION OF THE INVENTION

Figure 1:
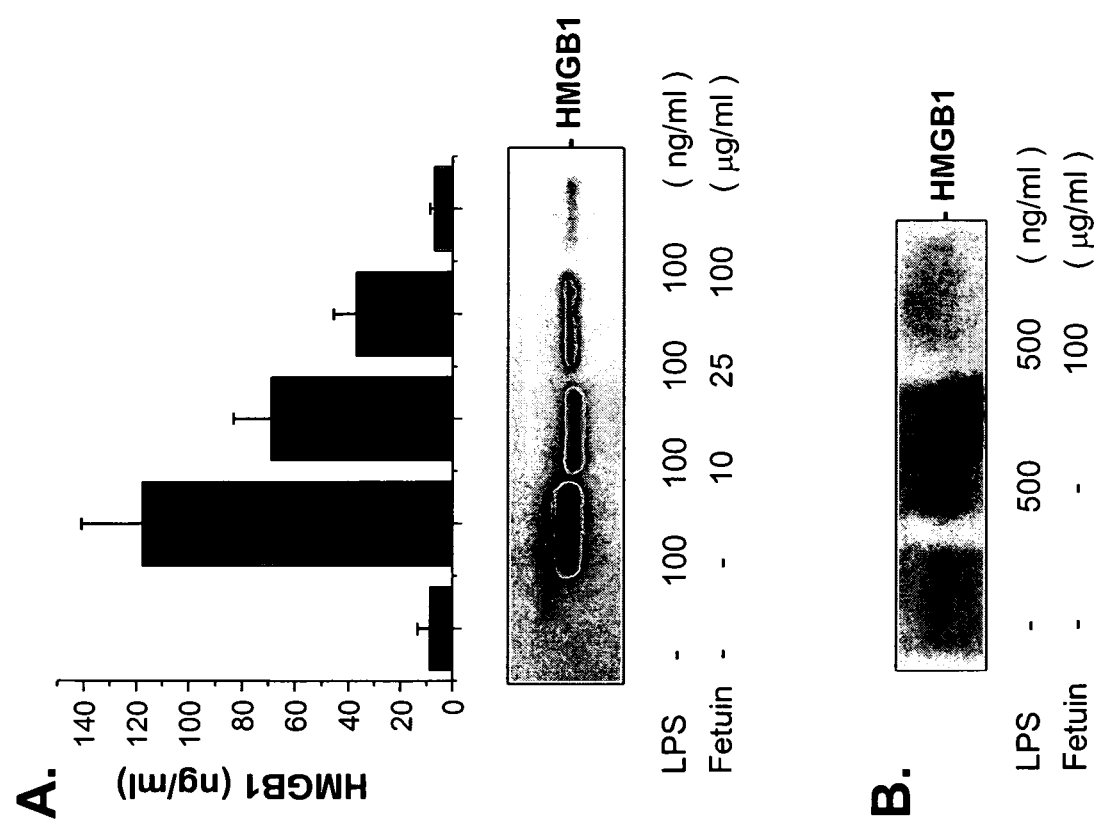
FIG. 1 is a graph and photographs of western blots establishing that fetuin inhibits HMGB1 release in LPS-induced cultures of murine macrophage-like RAW 264.7 cells (Panel A) or primary peripheral blood mononuclear cells (HuPBMCs, Panel B). Murine macrophage-like RAW 264.7 cells or HuPBMCs were stimulated with bacterial endotoxin for 16 hours, and assayed for HMGB1 accumulation in the culture medium by Western blotting analysis. Shown in the bar graph of panel A is the mean±S.E.M. of two independent experiments. Shown in the gel pictures are representative western blots.

The present invention is based on the discovery that fetuin inhibits release of HMGB1 by mammalian cells, and that this inhibition can be used to inhibit an inflammatory cytokine cascade induced by HMGB1 in a mammal. See Examples for experimental data related to this finding.

Accordingly, in some embodiments, the invention is directed to methods of inhibiting HMGB1 release by a mammalian cell. The methods comprise treating the cell with sufficient fetuin to inhibit HMGB1 release.

These methods can be utilized with any mammalian cell that produces HMGB1, including, but not limited to, pituicytes, macrophages, monocytes, neutrophils, fibroblasts, osteoblasts, smooth muscle cells, hepatocytes, epithelial cells, and neurons. In preferred embodiments, the cell is an immune cell, most preferably a macrophage or a monocyte.

These methods can be used on cells in culture, for example primary cultures or established cell lines. In preferred embodiments, however, the cell is part of a living mammal, most preferably a human suffering from, or at risk for, a condition mediated by an inflammatory cytokine cascade. Nonlimiting examples of these conditions are appendicitis, peptic, gastric and duodenal ulcers, peritonitis, pancreatitis, ulcerative, pseudomembranous, acute and ischemic colitis, diverticulitis, epiglottitis, achalasia, cholangitis, cholecystitis, hepatitis, Crohn's disease, enteritis, Whipple's disease, asthma, allergy, anaphylactic shock, immune complex disease, organ ischemia, reperfusion injury, organ necrosis, hay fever, sepsis, septicemia, endotoxic shock, cachexia, hyperpyrexia, eosinophilic granuloma, granulomatosis, sarcoidosis, septic abortion, epididymitis, vaginitis, prostatitis, urethritis, bronchitis, emphysema, rhinitis, cystic fibrosis, pneumonitis, pneumoultramicroscopicsilicovolcanoconiosis, alvealitis, bronchiolitis, pharyngitis, pleurisy, sinusitis, influenza, respiratory syncytial virus infection, herpes infection, HIV infection, hepatitis B virus infection, hepatitis C virus infection, disseminated bacteremia, Dengue fever, candidiasis, malaria, filariasis, amebiasis, hydatid cysts, burns, dermatitis, dermatomyositis, sunburn, urticaria, warts, wheals, vasulitis, angiitis, endocarditis, arteritis, atherosclerosis, thrombophlebitis, pericarditis, myocarditis, myocardial ischemia, periarteritis nodosa, rheumatic fever, Alzheimer's disease, coeliac disease, congestive heart failure, adult respiratory distress syndrome, meningitis, encephalitis, multiple sclerosis, cerebral infarction, cerebral embolism, Guillame-Barre syndrome, neuritis, neuralgia, spinal cord injury, paralysis, uveitis, arthritides, arthralgias, osteomyelitis, fasciitis, Paget's disease, gout, periodontal disease, rheumatoid arthritis, synovitis, myasthenia gravis, thryoiditis, systemic lupus erythematosus, Goodpasture's syndrome, Behcets's syndrome, allograft rejection, graft-versus-host disease, ankylosing spondylitis, Berger's disease, Type I diabetes, Retier's syndrome, and Hodgkins disease.

In preferred embodiments, the condition is appendicitis, peptic, gastric and duodenal ulcers, peritonitis, pancreatitis, ulcerative, pseudomembranous, acute and ischemic colitis, hepatitis, Crohn's disease, asthma, allergy, anaphylactic shock, organ ischemia, reperfusion injury, organ necrosis, hay fever, sepsis, septicemia, endotoxic shock, cachexia, septic abortion, disseminated bacteremia, burns, Alzheimer's disease, coeliac disease, congestive heart failure, adult respiratory distress syndrome, cerebral infarction, cerebral embolism, spinal cord injury, paralysis, allograft rejection or graft-versus-host disease. In most preferred embodiments, the condition is endotoxic shock.

Any mammalian fetuin can be used in these embodiments, including human fetuin (also known as $\alpha_2$-HS-glycoprotein). The skilled artisan would expect any mammalian fetuin to inhibit HMGB1 from any mammalian cell, including fetuin B, since fetuins from mammals have a high degree of homology. See, e.g., the rat, cow and human fetuin and fetuin B amino acid sequences provided in GenBank Accession Nos. NP 037030, NP 445800, NP 776409, NP 001613 and NP 0055190. Note also that bovine fetuin inhibited HMGB1 release in murine macrophages in Example 1. In preferred embodiments, the fetuin is from the same species as the cell.

In other embodiments, the invention is directed to methods of inhibiting an inflammatory cytokine cascade in a mammal. The methods comprise administering sufficient fetuin to the mammal to inhibit HMGB1 release in the mammal. Preferably, the mammal is a human suffering from, or at risk for, a condition mediated by an inflammatory cytokine cascade. As with previous embodiments, nonlimiting examples of such conditions include appendicitis, peptic, gastric and duodenal ulcers, peritonitis, pancreatitis, ulcerative, pseudomembranous, acute and ischemic colitis, diverticulitis, epiglottitis, achalasia, cholangitis, cholecystitis, hepatitis, Crohn's disease, enteritis, Whipple's disease, asthma, allergy, anaphylactic shock, immune complex disease, organ ischemia, reperfusion injury, organ necrosis, hay fever, sepsis, septicemia, endotoxic shock, cachexia, hyperpyrexia, eosinophilic granuloma, granulomatosis, sarcoidosis, septic abortion, epididymitis, vaginitis, prostatitis, urethritis, bronchitis, emphysema, rhinitis, cystic fibrosis, pneumonitis, pneumoultramicroscopicsilicovolcanoconiosis, alvealitis, bronchiolitis, pharyngitis, pleurisy, sinusitis, influenza, respiratory syncytial virus infection, herpes infection, HIV infection, hepatitis B virus infection, hepatitis C virus infection, disseminated bacteremia, Dengue fever, candidiasis, malaria, filariasis, amebiasis, hydatid cysts, burns, dermatitis, dermatomyositis, sunburn, urticaria, warts, wheals, vasulitis, angiitis, endocarditis, arteritis, atherosclerosis, thrombophlebitis, pericarditis, myocarditis, myocardial ischemia, periarteritis nodosa, rheumatic fever, Alzheimer's disease, coeliac disease, congestive heart failure, adult respiratory distress syndrome, meningitis, encephalitis, multiple sclerosis, cerebral infarction, cerebral embolism, Guillame-Barre syndrome, neuritis, neuralgia, spinal cord injury, paralysis, uveitis, arthritides, arthralgias, osteomyelitis, fasciitis, Paget's disease, gout, periodontal disease, rheumatoid arthritis, synovitis, myasthenia gravis, thryoiditis, systemic lupus erythematosus, Goodpasture's syndrome, Behcets's syndrome, allograft rejection, graft-versus-host disease, Type I diabetes, ankylosing spondylitis, Berger's disease, Retier's syndrome, and Hodgkins disease. Preferably, the condition is appendicitis, peptic, gastric and duodenal ulcers, peritonitis, pancreatitis, ulcerative, pseudomembranous, acute and ischemic colitis, hepatitis, Crohn's disease, asthma, allergy, anaphylactic shock, organ ischemia, reperfusion injury, organ necrosis, hay fever, sepsis, septicemia, endotoxic shock, cachexia, septic abortion, disseminated bacteremia, burns, Alzheimer's disease, coeliac disease, congestive heart failure, adult respiratory distress syndrome, cerebral infarction, cerebral embolism, spinal cord injury, paralysis, allograft rejection or graft-versus-host disease. In the most preferred embodiments, the condition is endotoxic shock.

In preferred embodiments, the fetuin is administered to the mammal within 8 hours of induction of an early mediator of the inflammatory cytokine cascade. Preferred examples of early mediators of the inflammatory cytokine cascade for these embodiments are tumor necrosis factor (TNF), interleukin (IL)-1β, IL-6, and IL-18.

As with the previous embodiments, any mammalian fetuin would be expected to inhibit HMGB1 in cells of any species. However, the fetuin is preferably from the same species as the mammal.

The fetuin compositions useful for these embodiments can be formulated without undue experimentation for administration to a mammal, including humans, as appropriate for any particular application. Additionally, proper dosages of the compositions can be determined without undue experimentation using standard dose-response protocols.

Accordingly, the fetuin compositions designed for oral, lingual, sublingual, buccal and intrabuccal administration can be made without undue experimentation by means well known in the art, for example with an inert diluent or with an edible carrier. The compositions may be enclosed in gelatin capsules or compressed into tablets. For the purpose of oral therapeutic administration, the pharmaceutical compositions of the present invention may be incorporated with excipients and used in the form of tablets, troches, capsules, elixirs, suspensions, syrups, wafers, chewing gums and the like.

Tablets, pills, capsules, troches and the like may also contain binders, recipients, disintegrating agent, lubricants, sweetening agents, and flavoring agents. Some examples of binders include microcrystalline cellulose, gum tragacanth or gelatin. Examples of excipients include starch or lactose. Some examples of disintegrating agents include alginic acid, corn starch and the like. Examples of lubricants include magnesium stearate or potassium stearate. An example of a glidant is colloidal silicon dioxide. Some examples of sweetening agents include sucrose, saccharin and the like. Examples of flavoring agents include peppermint, methyl salicylate, orange flavoring and the like. Materials used in preparing these various compositions should be pharmaceutically pure and nontoxic in the amounts used.

The fetuin compositions useful for the present invention can easily be administered parenterally such as for example, by intravenous, intramuscular, intrathecal or subcutaneous injection. Parenteral administration can be accomplished by incorporating the compositions of the present invention into a solution or suspension. Such solutions or suspensions may also include sterile diluents such as water for injection, saline solution, fixed oils, polyethylene glycols, glycerine, propylene glycol or other synthetic solvents. Parenteral formulations may also include antibacterial agents such as for example, benzyl alcohol or methyl parabens, antioxidants such as for example, ascorbic acid or sodium bisulfite and chelating agents such as EDTA. Buffers such as acetates, citrates or phosphates and agents for the adjustment of tonicity such as sodium chloride or dextrose may also be added. The parenteral preparation can be enclosed in ampules, disposable syringes or multiple dose vials made of glass or plastic.

Rectal administration includes administering the pharmaceutical compositions into the rectum or large intestine. This can be accomplished using suppositories or enemas. Suppository formulations can easily be made by methods known in the art. For example, suppository formulations can be prepared by heating glycerin to about 120° C., dissolving the composition in the glycerin, mixing the heated glycerin after which purified water may be added, and pouring the hot mixture into a suppository mold.

Transdermal administration includes percutaneous absorption of the composition through the skin. Transdermal formulations include patches (such as the well-known nicotine patch), ointments, creams, gels, salves and the like.

The present invention includes nasally administering to the mammal a therapeutically effective amount of the composition. As used herein, nasally administering or nasal administration includes administering the composition to the mucous membranes of the nasal passage or nasal cavity of the patient. As used herein, pharmaceutical compositions for nasal administration of a composition include therapeutically effective amounts of the composition prepared by well-known methods to be administered, for example, as a nasal spray, nasal drop, suspension, gel, ointment, cream or powder. Administration of the composition may also take place using a nasal tampon or nasal sponge.

It is anticipated that, for many embodiments, it would be desired that the fetuin be administered parenterally, preferably, intravenously, to introduce the fetuin into the bloodstream as quickly as possible, to achieve the maximum anti-inflammatory effect.

In related embodiments, the invention is directed to methods of treating a condition in a mammal characterized by an inflammatory cytokine cascade. The methods comprise administering sufficient fetuin to the mammal to inhibit HMGB1 release in the mammal.

As with previous embodiments, nonlimiting examples of conditions that can be treated with these methods include appendicitis, peptic, gastric and duodenal ulcers, peritonitis, pancreatitis, ulcerative, pseudomembranous, acute and ischemic colitis, diverticulitis, epiglottitis, achalasia, cholangitis, cholecystitis, hepatitis, Crohn's disease, enteritis, Whipple's disease, asthma, allergy, anaphylactic shock, immune complex disease, organ ischemia, reperfusion injury, organ necrosis, hay fever, sepsis, septicemia, endotoxic shock, cachexia, hyperpyrexia, eosinophilic granuloma, granulomatosis, sarcoidosis, septic abortion, epididymitis, vaginitis, prostatitis, urethritis, bronchitis, emphysema, rhinitis, cystic fibrosis, pneumonitis, pneumoultramicroscopicsilicovolcanoconiosis, alvealitis, bronchiolitis, pharyngitis, pleurisy, sinusitis, influenza, respiratory syncytial virus infection, herpes infection, HIV infection, hepatitis B virus infection, hepatitis C virus infection, disseminated bacteremia, Dengue fever, candidiasis, malaria, filariasis, amebiasis, hydatid cysts, burns, dermatitis, dermatomyositis, sunburn, urticaria, warts, wheals, vasulitis, angiitis, endocarditis, arteritis, atherosclerosis, thrombophlebitis, pericarditis, myocarditis, myocardial ischemia, periarteritis nodosa, rheumatic fever, Alzheimer's disease, coeliac disease, congestive heart failure, adult respiratory distress syndrome, meningitis, encephalitis, multiple sclerosis, cerebral infarction, cerebral embolism, Guillame-Barre syndrome, neuritis, neuralgia, spinal cord injury, paralysis, uveitis, arthritides, arthralgias, osteomyelitis, fasciitis, Paget's disease, gout, periodontal disease, rheumatoid arthritis, synovitis, myasthenia gravis, thryoiditis, systemic lupus erythematosus, Goodpasture's syndrome, Behcets's syndrome, allograft rejection, graft-versus-host disease, Type I diabetes, ankylosing spondylitis, Berger's disease, Retier's syndrome, and Hodgkins disease. Preferably, the condition is appendicitis, peptic, gastric and duodenal ulcers, peritonitis, pancreatitis, ulcerative, pseudomembranous, acute and ischemic colitis, hepatitis, Crohn's disease, asthma, allergy, anaphylactic shock, organ ischemia, reperfusion injury, organ necrosis, hay fever, sepsis, septicemia, endotoxic shock, cachexia, septic abortion, disseminated bacteremia, burns, Alzheimer's disease, coeliac disease, congestive heart failure, adult respiratory distress syndrome, cerebral infarction, cerebral embolism, spinal cord injury, paralysis, allograft rejection or graft-versus-host disease. Most preferably, the condition is endotoxic shock.

As with the previous embodiments, any mammalian fetuin would be expected to inhibit HMGB1 in cells of any species. However, the fetuin is preferably from the same species as the mammal. Also as with previous embodiments, parenteral administration, for example intravenous administration, is preferred in many applications.

Preferred embodiments of the invention are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the examples.

EXAMPLE 1

Inhibition of HMGB1 Release from Mammalian Cells by Fetuin

Example Summary

Gram-negative bacterial infection and systemic inflammation are widespread problems in critically ill patients. A product of Gram-negative bacteria, endotoxin (lipopolysaccharide, LPS), stimulates macrophages to release excess amounts of proinflammatory cytokines (such as TNF and IL-1) during overwhelming infection. If delivered early enough, anti-TNF therapy can be effective in animal models of systemic inflammation, but early treatment is difficult to achieve in humans. An alternative therapeutic strategy would be to identify "late" macrophage mediators that may be clinically more accessible. We recently discovered that a ubiquitous protein, HMGB1, is released late by activated macrophages, and functions as a late mediator of endotoxin lethality. Fetuin (fetus protein in Greek) was first identified by Pederson as a major fetal plasma protein more than fifty years ago, and subsequently characterized as a liver-derived negative acute phase protein. OBJECTIVES: To elucidate the roles of fetuin in the regulation of innate immune response, we examined the effect of fetuin on HMGB1 release in cultures of both murine macrophage-like RAW 264.7 cells and human peripheral blood mononuclear cells (HuPBMCs). METHODS: Macrophage-like RAW 264.7 cells or HuPBMCs were cultured in low serum OPTI-MEM I medium until 80-90% confluence, and stimulated with LPS (100 ng/ml) either alone, or in the presence of fetuin at various concentrations (0, 10, 25, and 100 micrograms/ml). At 16 hours after LPS stimulation, the levels of HMGB1 in the culture medium were determined. RESULTS: Fetuin dose-dependently attenuated LPS-induced HMGB1 release in cultures of both murine macrophages or human monocytes. Similarly, fetuin promoted a dose-dependent inhibition of HMGB1 release induced by proinflammatory cytokines such as TNF and IFN-$\gamma$. CONCLUSIONS: Fetuin, occupies an important role in the regulation of the innate immune response in endotoxemia. Supplementation of exogenous fetuin holds potential as a therapeutically effective treatment of lethal systemic inflammation (e.g., endotoxemia, and sepsis).

Materials and Methods

Cell Culture. Murine macrophage-like RAW 264.7 cells were obtained from the American Type Culture Collection (ATCC, Rockville, Md.) and cultured in RPMI 1640 medium (Gibco BRL, Grand Island, N.Y.) supplemented with 10% fetal bovine serum (FBS) and 2 mM glutamine. At 80-90% confluency, RAW 264.7 cells were washed twice with, and subsequently cultured in, serum-free OPTI-MEM I medium (Gibco BRL, Grand Island, N.Y.). After pre-incubation for two hours, cell cultures were stimulated with various stimuli (IL-6, Cat. # 1 444 581; IFN-<, Cat. #1 276 905, Roche). In some treatments, bovine fetuin (Calbiochem, La Jolla, Calif.) was also added. Human peripheral blood mononuclear cells (HuPBMCs) were isolated by density gradient centrifugation through Ficoll (Ficoll-Paque PLUS, Pharmacia, Piscataway, N.J.) as previously described (Wang et al., 1998) and cultured in RPMI 1640/10% heat-inactivated human serum/2 mM L-glutamine for overnight. Nonadherent cells were subsequently removed, and adherent monocyte-enriched cultures were stimulated with IFN-$\gamma$ or LPS. In some treatments, human fetuin (Calbiochem) was also added.

Immunoassays for HMGB1. The levels of HMGB1 in the culture medium or macrophage cells were assayed by Western blotting analysis using rabbit polyclonal antibodies as previously described (Wang et al. 1999a). Western blots were scanned with a silver image scanner (Silverscaner II, Lacie Limited, Beaverton, Oreg.), and the relative band intensity was quantified by using the NIH image 1.59 software. The levels of HMGB1 were calculated with reference to standard curves generated with purified rHMGB1.

Statistical Analysis. Values in the figures were expressed as mean±S.E.M. of 2-3 independent experiments either in duplicates or triplicates (n=6-9). Student's two-tailed t-test was used to compare means between groups. A P-value less than 0.05 was considered to be statistically significant.

Results

Effect of fetuin on HMGB1 release. To evaluate the effect of fetuin in inhibiting HMGB1 release, cultures of macrophage-like RAW 264.7 cells were stimulated with bacterial endotoxin (lipopolysacharide, 1PS) or proinflammtory cytokines (IFN-γ and TNF), and levels of HMGB1 in the culture medium were subsequently measured by immunoblotting analysis. HMGB1 was barely detected in the culture medium in the absence of inflammatory stimuli ("-"), but was detected after stimulation of cells with bacterial endotoxin (FIG. 1A). Administration of fetuin dose-dependently suppressed LPS-induced HMGB1 release by murine macrophage cell cultures. The fetuin-mediated suppression of HMGB1 release was further confirmed in primary HuPB-MCs (FIG. 1B). Again, fetuin significantly inhibited LPS-induced HMGB1 release by human peripheral blood mononuclear cells. Thus, fetuin effectively inhibited LPS-induced HMGB1 release in both macrophage and monocyte cell cultures.

Figure 2:
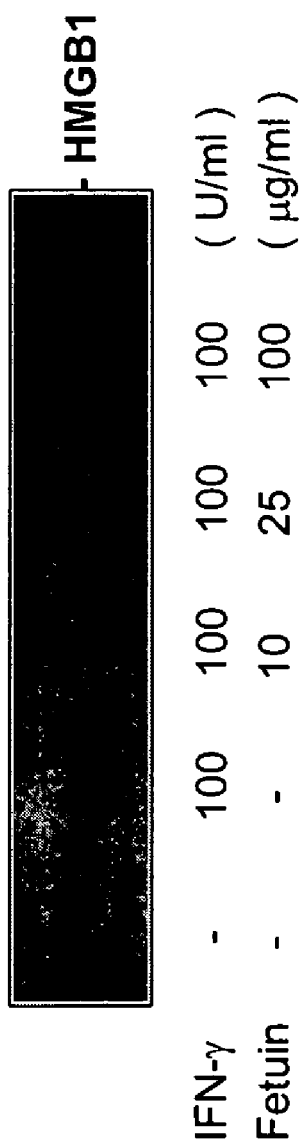
FIG. 2 is a photograph of a western blot establishing that fetuin inhibits HMGB1 release in IFN-γ-induced cultures of murine macrophage-like RAW 264.7 cells. RAW 264.7 cells were stimulated with IFN-γ, either alone or in the presence of fetuin at various concentrations for 16 hours. The levels of HMGB1 in the culture medium were assayed at 16 hours post stimulation by Western blotting analysis.
Figure 3:
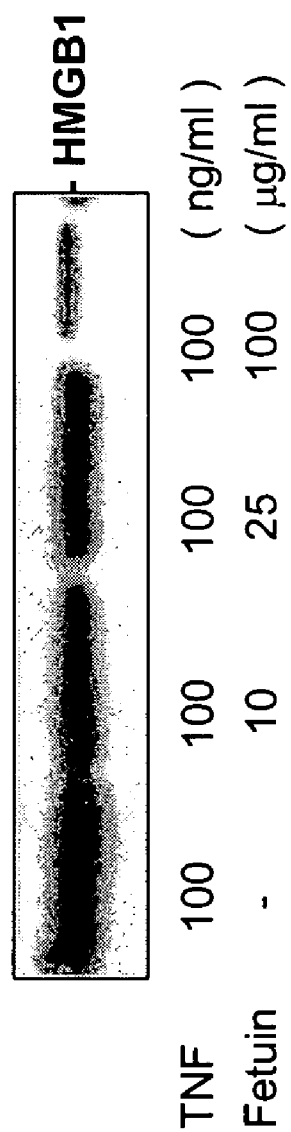
FIG. 3 is a photograph of a western blot establishing that fetuin inhibits HMGB1 release in TNF-induced cultures of murine macrophage-like RAW 264.7 cells. RAW 264.7 cells were stimulated with TNF, either alone or in the presence of fetuin at various concentrations for 16 hours. The levels of HMGB1 in the culture medium were assayed at 16 hours post stimulation by western blotting analysis.

We also examined the effect of fetuin on HMGB1 release induced by proinflammtory cytokines such as IFN-γ (FIG. 2) and TNF (FIG. 3). Similarly, fetuin promoted a dose-dependent suppression of HMGB1 release induced by endogenous proinflammatory cytokines (such as IFN-γ and TNF), indicating that fetuin occupies an important role in the regulation of HMGB1 release by innate immune cells.

Figure 4:
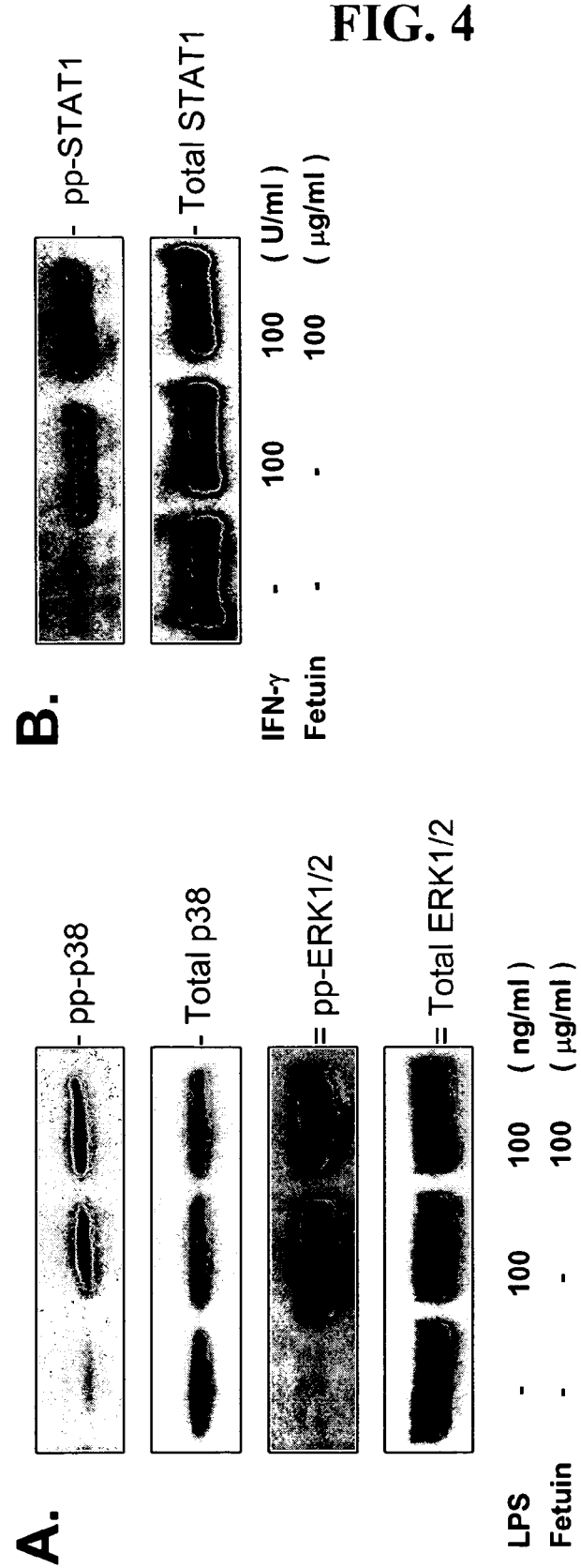
FIG. 4 are photographs of western blots establishing that fetuin has no effect on phosphorylation of STAT1 and MAP kinases (p38, ERK1/2, and JNK). RAW 264.7 cell cultures were stimulated with LPS or IFN-γ 30 minutes, and the concentrations of phospho-MAP kinases (Panel A) and phospho-STAT1 (Panel B) were determined by western blotting analysis using specific antibodies.
Figure 5:
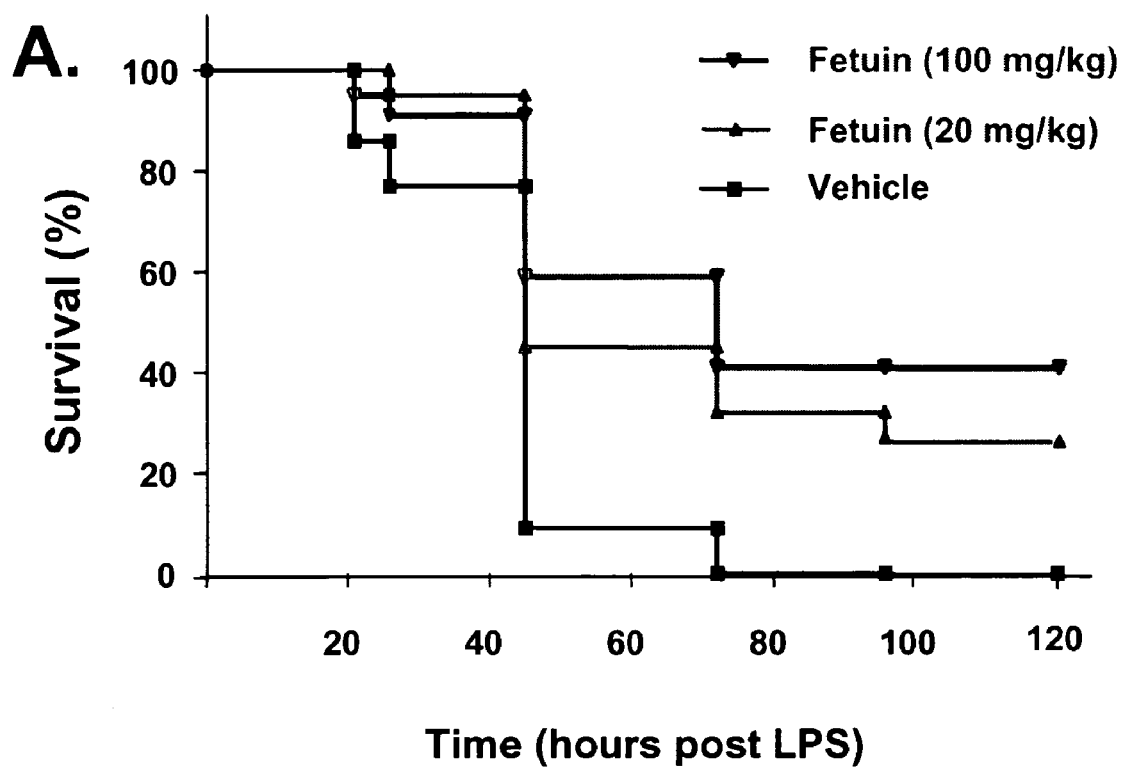
FIG. 5 is a graph and a photograph of a western blot demonstrating that administration of fetuin attenuates the lethality of endotoxemia. Panel A is a graph of experimental results where mice (N=20 per group) received a lethal infusion of endotoxin (LPS, 10 mg/kg, i.p.) and were treated with fetuin at −0.5, +24, and +48 hours later. Fetuin conferred significant protection against endotoxemic lethality (P<0.05, as measured by Fisher's exact test). Panel B shows the results of a parallel experiment, where serum was collected from five normal ("Control"), vehicle-treated endotoxemic ("LPS"), or fetuin-treated endotoxemic ("LPS+Fetuin") at 24 hours after endotoxemia, and assayed for HMGB1 levels by western blot analysis. Panel B shows a representative western blot of serum pooled from five mice in each group.
Figure 5:
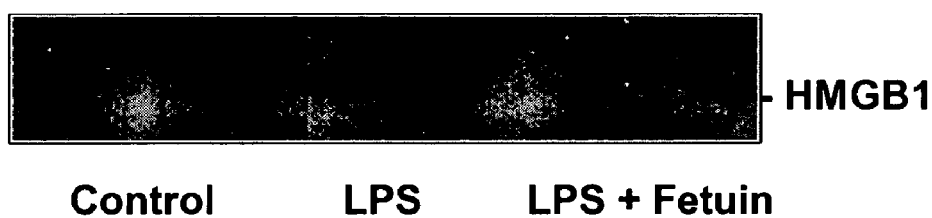

Effects of fetuin on phosphorylation of MAPKs and STAT1. It has been well demonstrated that IFN-γ and bacterial endotoxin (LPS) utilize different signal transduction pathways to activate macrophages. To examine the mechanisms of fetuin-mediated HMGB1 suppression, we examined the effects of fetuin on phosphorylation of various MAPK kinases and STAT1 in macrophage cultures. As expected, LPS, but not IFN-γ, induced a significant phosphorylation of p38, MEK1/2, and p44/42 (ERK1/2) (FIG. 5A). In contrast, IFN-γ, but not LPS, triggered specific phosphorylation of STAT1 (Tyr701) at concentrations that were also effective in inducing HMGB1 release (FIG. 4B). Fetuin, at concentrations that effectively inhibited HMGB1 release, did not affect the phosphorylation status of either MAPK (P38 and ERK1/2, FIG. 4A) or STAT1 (FIG. 4B). This suggests that fetuin specifically inhibit HMGB1 release in MAPK- and STAT1-independent mechanisms.

EXAMPLE 2

Inhibition of Lethal Endotoxemia In Vivo by Fetuin

Example Summary

Sepsis, a potentially fatal clinical syndrome, is partly mediated by a late proinflammatory cytokine HMGB1. Here, we report that intraperitoneal administration of an anti-inflammatory protein, fetuin, attenuates lethal endotoxemia, partly through inhibiting systemic accumulation of HMGB1. In animal model of sepsis, delayed fetuin administration at 24 h after cecal ligation and puncture significantly increased survival (vehicle survival=45% vs. fetuin survival=90%, $P<0.05$).

Material and Methods

Animals. Male 6- to 8-week-old Balb/C mice (20-25 g) were purchased from Harlan-Sprague-Dawley and allowed to acclimate for 7 days housed at 25° C. on a 12-h light 12-h dark cycle. Animals were grouped randomly and assigned to a specific experiment. All animal experiments were performed in accordance with the National Institutes of Health Guidelines under protocols approved by the Institutional Animal Care and Use Committee of North Shore University Hospital.

Endotoxin Shock. Mice were intraperitoneally injected with endotoxin (*Escherichia coli* LPS 0111:B4; Sigma, 10 mg/kg), and monitored for survival for up to two weeks. In parallel experiments, blood was collected at 24 hours after LPS administration, and serum HMGB1 levels were determined by Western blotting analysis as previously described (Wang et al., 1999).

Cecal Ligation and Puncture. Cecal ligation and puncture was performed as previously described (Yang, H., et al, 2004). Briefly, mice were anesthetized with ketamine (100 mg/kg, i.m.) and xylazine (10 mg/kg, i.m.), a midline incision was performed, and the cecum was isolated. A 6-0 prolene suture ligature was placed at a level 5.0 mm from the cecal tip away from the leocecal valve. The ligated cecal stump then was punctured once with a 22-gauge needle, and stool was extruded (1 mm) to ascertain patency of the puncture site. The cecum then was placed back into its normal intraabdominal position, and the abdomen was closed with a running suture of 6-0 prolene in two layers, peritoneum and fascia separately, to prevent leakage of fluid. All animals received an antibiotic (primaxin; 0.5 mg/kg s.c.) 12 h after surgery as a single dose. All animals received resuscitation with normal saline 24 h after surgery as a single injection (20 ml/kg of body weight). Mortality was recorded for up to 2 week after the procedure; survivors were followed for 2 weeks to ensure no late mortalities had occurred.

Results

Fetuin prevents endotoxin lethality partly through inhibiting HMGB1 release. We first evaluated the efficacy of fetuin as a therapeutic agent for systemic inflammation in a standard model of murine endotoxemia. Balb/C mice were intraperitoneally administered with the first dose of fetuin (20, 200 mg/kg) at 30 minutes before LPS administration (10 mg/kg). Additional doses of fetuin were repeatedly administered at +24 and +48 hours after LPS administration. Administration of fetuin significantly increased animal survival rate from 0% in vehicle control group to 40% in fetuin-treated group (FIG. 5A). Late death in fetuin-treated animals was not observed up to 2 weeks, indicating that fetuin treatment conferred a long lasting protection against lethal endotoxemia. Accordingly, fetuin administration significantly attenuated systemic accumulation of HMGB1 in endoxemic mice (FIG. 5B).

Figure 6:
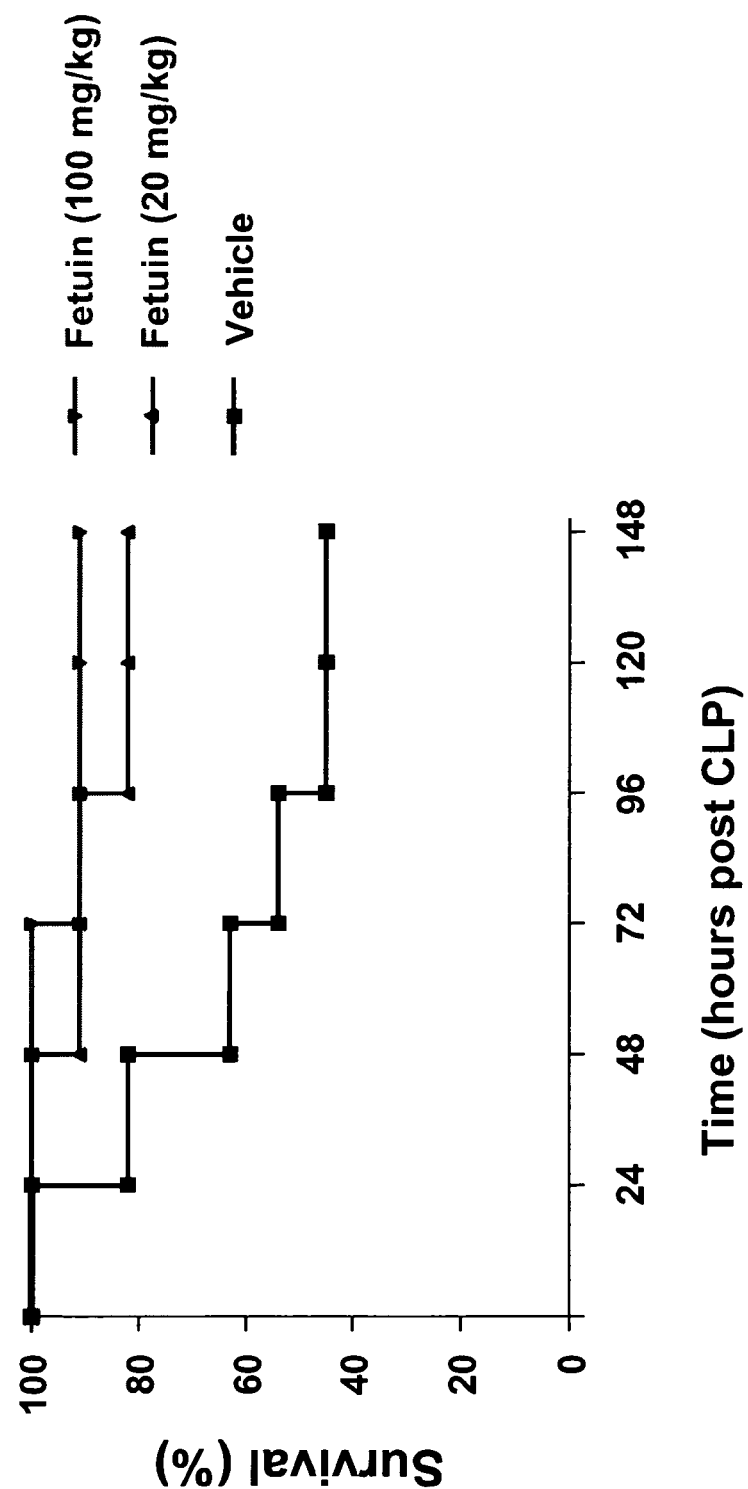
FIG. 6 is a graph of experimental results demonstrating that delayed administration of fetuin attenuates lethal sepsis. The cecal ligation and puncture technique was used to induce intraabdominal sepsis in mice (N=11 per group). Repeated administration of fetuin (at the doses indicated) at +24, and +48 hours after cecal ligation and puncture increased survival from 45% in vehicle-treated control group to 90% in fetuin-treated group.

Delayed administration of fetuin prevents lethality of sepsis. We further evaluated the efficacy of fetuin in preventing lethal sepsis in a standardized model of peritonitis induced by surgical perforation of the cecum. Mice subjected to peritonitis received either vehicle or fetuin beginning 24 h after the onset of peritonitis, a time at which 10% of the mice in each group already had died. Treatment with fetuin beginning 24 h after CLP surgery significantly increased survival (survival in vehicle-treated controls=45% vs. survival in fetuin-treated group=90%, N=11 mice per group, FIG. 6). All animals were observed for at least 2 weeks and late deaths did not occur, indicating that fetuin antibody did not merely delay death but conferred lasting protection against lethal sepsis. Administration of fetuin at this late stage in disease progression "rescued" animals from the lethal sequelae of sepsis, because animals in both the fetuin- and vehicle-treated groups had already begun to succumb at the time of the first fetuin administration.

In view of the above, it will be seen that the several advantages of the invention are achieved and other advantages attained.

As various changes could be made in the above methods and compositions without departing from the scope of the invention, it is intended that all matter contained in the above description and shown in the accompanying drawings shall be interpreted as illustrative and not in a limiting sense.

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

What is claimed is:

1. A method for treating sepsis or septicemia in a mammal having sepsis or septicemia, the method comprising administering to the mammal after the onset of sepsis or septicemia an amount of fetuin effective to treat sepsis or septicemia in the mammal.

2. The method of claim 1, wherein the mammal has sepsis.

3. The method of claim 1, wherein the mammal has septicemia.

4. The method of claim 1, wherein fetuin is administered to the mammal within 8 hours after the onset of sepsis or septicemia.

5. The method of claim 1, wherein fetuin is administered within 24 hours after the onset of sepsis or septicemia.

6. The method of claim 1, wherein fetuin is administered parenterally.

7. The method of claim 1, wherein fetuin is administered intravenously.

8. The method of claim 1, wherein the mammal is a human.

* * * * *